(12) United States Patent
Prestidge et al.

(10) Patent No.: US 6,746,420 B1
(45) Date of Patent: Jun. 8, 2004

(54) PARENTERAL APPARATUS (76) Inventors: Dean B. Prestidge, 7 Key West Drive, Mulaloo, Western Australia 6027 (AU); Maxwell E. Whisson, 5/70 Subiaco Road, Subiaco, Western Australia 6008 (AU)

( * ) Notice: Subject to any disclaimer, the term of this patent is extended or adjusted under 35 U.S.C. 154(b) by 0 days.

(21) Appl. No.: 09/857,988
(22) PCT Filed: Dec. 10, 1999
(86) PCT No.: PCT/AU99/01093
§ 371 (c)(1), (2), (4) Date: Jun. 8, 2001
(87) PCT Pub. No.: WO00/35518
PCT Pub. Date: Jun. 22, 2000

(30) Foreign Application Priority Data

Dec. 11, 1998  (AU) .............................................. PP7660

(51) Int. Cl.⁷ .............................................. A61M 31/00
(52) U.S. Cl. .................. 604/48; 604/158; 604/227; 604/181; 604/164.08; 604/164.01; 604/164.12
(58) Field of Search ...................... 604/48, 164, 164.01, 604/165.01, 164.08, 164.09, 165.03, 158, 164.02, 164.11, 164.12, 218, 227–229, 235–237, 240, 241, 181, 194–196, 182, 184, 185, 187, 188

(56) References Cited

U.S. PATENT DOCUMENTS

| | | | | |
|---|---|---|---|---|
| 4,828,548 A | * | 5/1989 | Walter | 604/164 |
| 5,201,719 A | * | 4/1993 | Collins et al. | 604/195 |
| 5,407,431 A | * | 4/1995 | Botich et al. | 604/110 |
| 5,759,177 A | | 6/1998 | Whisson | |
| 5,795,339 A | * | 8/1998 | Erksine | 604/264 |
| 5,824,001 A | * | 10/1998 | Erksine | 604/158 |

FOREIGN PATENT DOCUMENTS

| | | |
|---|---|---|
| EP | 0 730 880 | 9/1996 |
| EP | 0 812 602 | 12/1997 |
| GB | 2324734 | 11/1998 |
| WO | 96/32981 | * 10/1996 |

* cited by examiner

Primary Examiner—Henry Bennett
Assistant Examiner—Camtu Nguyen
(74) Attorney, Agent, or Firm—Bachman & LaPointe, P.C.

(57) ABSTRACT

A parenteral apparatus (10, 50, 60, 70, 90, 110, 120) comprises a chamber (26) for parenteral fluid within a housing (12). The apparatus also includes an axially slidable seal (24) operatively associated with a needle (28) and a catheter (32) enclosing the needle (28) in part. In operation, the needle (28) makes an incision in tissue by means of a sharp point (33) and it is then withdrawn into the housing (12) whilst the catheter remains in contact with the tissue. The parenteral fluid is expelled by movement of the seal (24) from the chamber (26) through the needle (28) initially and subsequently through the needle (28) and the catheter (32) as the needle (28) is withdrawn.

17 Claims, 9 Drawing Sheets

PARENTERAL APPARATUS

FIELD OF THE INVENTION

The present invention relates to a parenteral apparatus.

PRIOR ART

Injection devices which use a sharp needle to enter human tissue are now widely recognized as being hazardous to users and other individuals because the sharp point, contaminated by its exposure to the tissue of the first person may penetrate the skin of a second person and in doing so may carry micro-organisms from the patient on whom the injection device was first used into the tissue of a second person. Such transmission may result in the development of disease in the second person. When the penetration of the skin is accidental it is referred to as "needlestick injury" or "needle-prick injury".

Disease transmission by this means is now recognised as a major cause of occupational disease transmission to healthcare workers. The prevention of such transmission has resulted in the setting up of expensive and inefficient procedures and has caused an increase in the cost of providing medical support.

Transmission of disease may also result from the deliberate re-use of a sharp needle by a second person and this is a major cause of transmission of such diseases as hepatitis C and AIDS (HIV) amongst users of narcotic intravenous drugs. Many other infectious diseases may be transmitted from one person to another by contaminated needles.

Three main strategies have been put in place to reduce the risk of disease transmission by contaminated needles. These are (i) strict adherence to methods and procedures which reduce the risk of accidental needlestick injury;

(ii) the widespread distribution of secure containers (sharps containers) into which the used needles can be placed as soon as possible after use; and (iii) the invention and development of injection devices whereby the sharp needle point can be covered soon after use, so reducing the risk of needlestick injury, and in many examples, reducing the possibility of the injection device being used a second time.

A disadvantage of all of these strategies is that they all cause some perturbation of optimal or most efficient clinical practice and all incur increased expense in providing medical care. Often these factors mean that the safety measures fail not because the device does not provide safety but simply because they are not put into universal practice. Most importantly, these strategies and techniques leave a "window of risk" in the interval between removing the contaminated needle from the tissue of a person and putting into effect the chosen procedure or technique to make the contaminated needle safe.

There is a second type of problem associated with the use of sharp tubular needles to obtain access to living tissues, especially veins or arteries. This second problem is that the sharp point is only necessary to advance the needle to the required location in the tissue. When in the desired location the sharp point is often a disadvantage.

The prior art also shows a great variety of methods of covering a sharp needle tip, such as a sheath moving forward to cover the needle after use, retraction of the needle into the body of the syringe or capture of the hub of the needle by a latch on the moving plunger after emptying the syringe. These methods are associated with varying degrees of complexity and interference with normal clinical requirements. Above all they do not allow the use of the device for the transfer of fluid to or from the living tissue after the sharp tip is covered and do not protect the living tissue from damage by the sharp tip during the parenteral procedure. An internal blunt tube within the sharp tubular needle overcomes many of these problems to a degree but has the disadvantages of significantly increasing the resistance to fluid flow and of not permitting the sharp needle point to be covered.

It is an object of the present invention to provide an apparatus which can be used in much the same way as conventional tubular injection needles and catheters for achieving fluid transfer between the exterior and the parenteral tissue of the living body and without requiring difficult or complex techniques to maintain fluid transfer passages during movement of the needle within the device.

BRIEF DESCRIPTION OF THE INVENTION

In accordance with one aspect of the present invention there is provided a parenteral apparatus characterised by a housing having a first end and a second end and defining a chamber for parenteral fluid, a thin walled catheter having a free end closely enclosing a tubular needle having a sharp point, the catheter being mounted to the housing, the needle and the catheter being longitudinally moveable relative to one another between a first position at which the needle extends from the catheter so that the sharp point is exposed and a second position at which the sharp point is located within the housing, the needle remaining in a fluid pathway of the parenteral apparatus at all times between the first and second positions, the sharp point of the needle being arranged to pierce tissue when the catheter and the needle are in their relative first position and retraction means being provided for moving the needle and catheter relatively from the first position.

BRIEF DESCRIPTION OF THE DRAWINGS

The present invention will now be described, by way of example, with reference to the accompanying drawings, in which.

The present invention will now be described in greater detail by reference to the accompanying drawings, in which the same numbers are used to refer to similar parts throughout.

In the descriptions which follow, "needle" means a thin walled stiff tube or C section such as a steel tube, sharpened at least at one end. "Catheter" means a thin walled flexible tube, attached at one end and free or capable of being made free at the other end and preferably formed of inert plastic elastomer which can be fitted closely but slidingly to an outer wall of a chosen needle. The mechanical properties of the needle and catheter may be optimised to suit particular applications and the hardness and stiffness may if desired be varied along the length. Both catheter and needle or catheter or needle may be formed of composite materials to suit particular applications.

It may be possible to deliver parenteral fluid to or from the catheter/needle complex in a number of ways and some of these are shown in the drawings.

Figure 1:
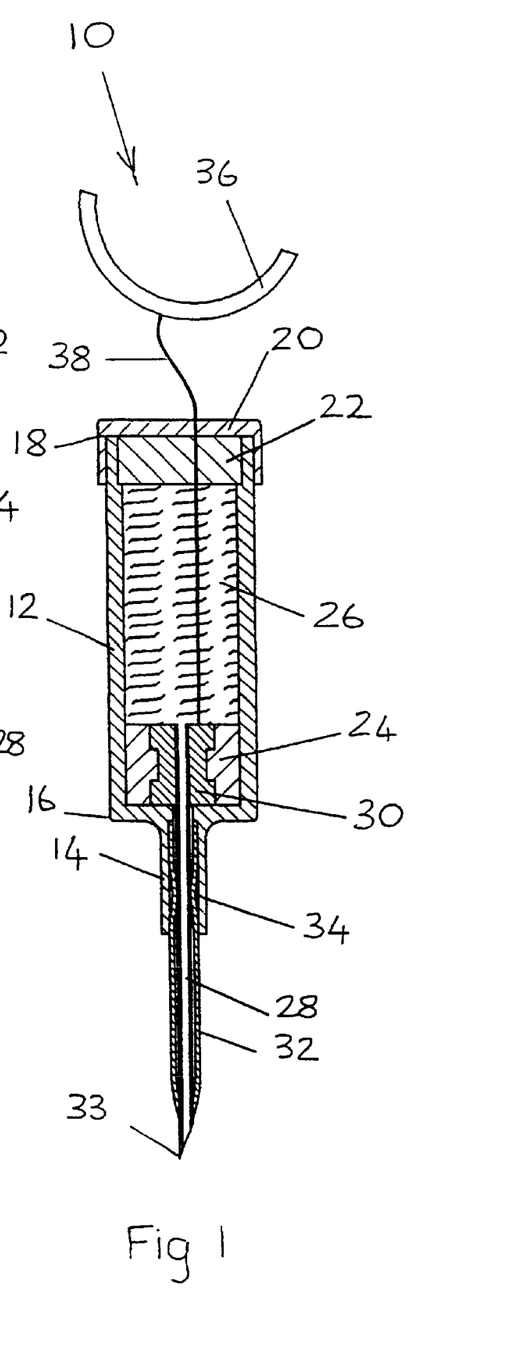
FIG. 1 is a longitudinal sectional view of a first embodiment of a parenteral apparatus in accordance with the present invention in a first position ready to perform an injection.
Figure 2:
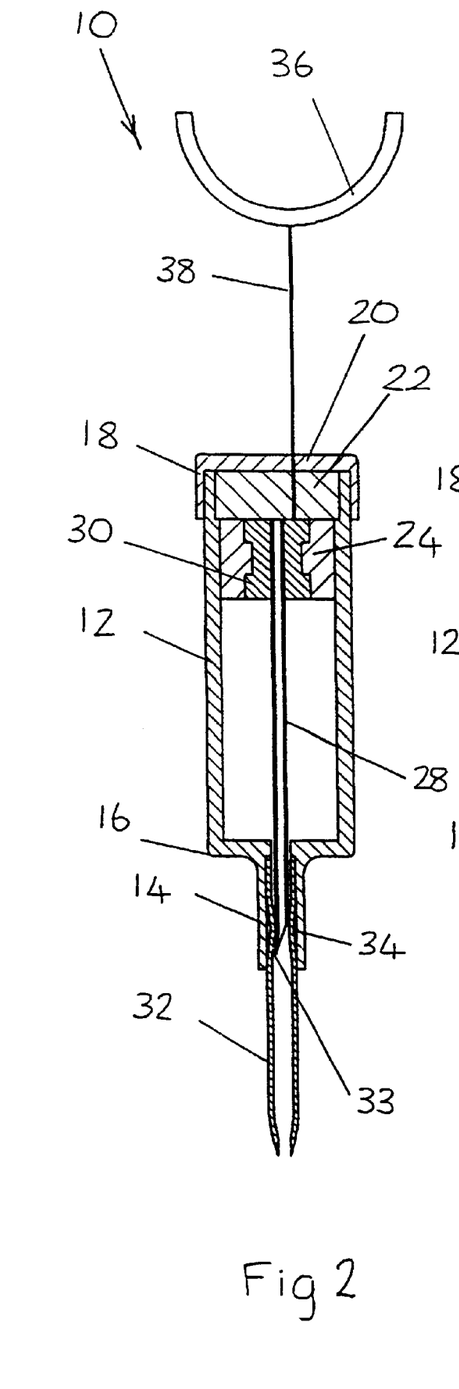
FIG. 2 is a view similar to FIG. 1 in which the parenteral apparatus is in a second position after completion of an injection.

In FIGS. 1 and 2 of the accompanying drawings there is shown a parenteral apparatus 10 having housing 12 in the form of a substantially tubular barrel opening to a forwardly projecting tubular boss 14 at a first end 16 and being closed at the second end 18 by a cap 20. A firmly fitting bung 22 and an axially slidable seal 24 are located within the body 12 and are spaced from one another. The bung 22 is located adjacent the cup 20 and the seal 24 is located adjacent the boss 14. The bung 22 and the seal 24 define between them a sealed chamber 26 as can be seen in FIG. 1. The bung 22 and the seal 24 are preferably formed from elastomers of suitable hardness. In the embodiment illustrated the bung 22 is not arranged to move axially in the housing 12 at all although it is envisaged that in some embodiments the bung 22 could be slidable although more resistant to sliding than the seal 24. Further, the bung 22 could be replaced by any of the convenient means for closing off the housing 12 such as an elastomer seal mounted on the cap 20 or a rear wall extending across the housing 12.

An injection needle 28 is fitted sealingly within and through the seal 24 preferably by means of a hard hub 30 fixed firmly to an outer surface of the needle adjacent an inner end thereof. The hub 30 is mounted within the seal 24 and mates with an internal profile of the seal 24 so as to be firmly engaged with the seal 24.

An elastic, flexible, thin walled catheter 32 has an inner end which is located within the boss 14 and which is firmly fixed to the boss 14. As shown in FIG. 1, in the position at which the parenteral apparatus 10 is ready for use, the needle 28 extends throughout the length of the catheter 32 and has a sharp outer end 33 projecting outwardly from an outer end of the catheter 32. The dimensions of the needle 28 and the catheter 32 are chosen so that the needle 28 can slide easily and sealingly within the catheter 32. A constriction 34 may be formed in the catheter 32 to assist sealing if desired. The needle 28 is preferably constructed from stainless steel tube sharpened at the outer end 33.

A handle means 36 is attached to an outer end of a flexible drawstring 38. The drawstring 38 passes freely through the end cap 20 and seal sealingly through the bung 22 and is firmly attached at an inner end to the hub 30.

In use, the apparatus 10 is initially in the condition shown in FIG. 1 with the chamber 26 filled with a parenteral fluid.

The outer end 33 of the needle 28 is caused to pierce parenteral tissue so that the needle 28 and the catheter 32 can enter the parenteral tissue. In order to inject the parenteral fluid into the tissue, the handle 36 is manually pulled so as to pull on the drawstring 38.

The drawstring 38 is thus caused to pull the hub 30 and the seal 24 axially away from the end 16 of the housing 12. As this takes place, the parenteral fluid in the chamber 26 is expelled through the needle 28 and the catheter 32 so as to enter the parenteral tissue. Further, movement of the hub 30 and the seal 24 to reach the second end 18 of the housing 12 causes the needle 28 to retract and move out of the parenteral tissue so that only the catheter 32 is disposed in the tissue. Eventually, the seal 24 reaches the position shown in FIG. 2 at which the seal 24 and the hub 30 abut the bung 22 and the needle 28 has been retracted to a point at which the outer end 33 is housed within the boss 14. The fluid path established by the needle 28 and the catheter 32 is maintained throughout until the injection of fluid is completed although after withdrawal of the needle 28 partially only the catheter 32 remains in contact with the tissue.

In the initial phase of the operation, the needle 28 is constrained from moving back in the body 12 by frictional force between the seal 24 and the housing 12, frictional force between the needle 28 and the catheter 32 and resistance of fluid flow from the chamber 26 through the needle 28. If desired, a more positive restraint may be utilized such as a ridge within the housing 12 at a location which slightly inhibits initial movement of the seal 24.

Further, it is envisaged that the apparatus 10 could be provided with small opening, similar to the opening 58 described hereinafter, to avoid the portion of the housing 12 between the seal 24 and the end 16 being airtight.

Figure 3:
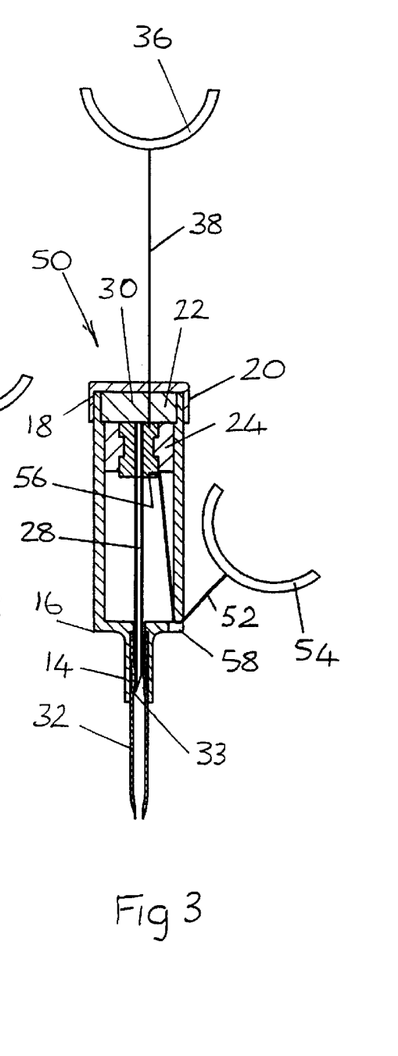
FIG. 3 is a longitudinal sectional view of a second embodiment of a parenteral apparatus in accordance with the present invention with a needle assembly retracted and ready to be moved to a further position during an action of filling the apparatus with parenteral fluid.
Figure 4:
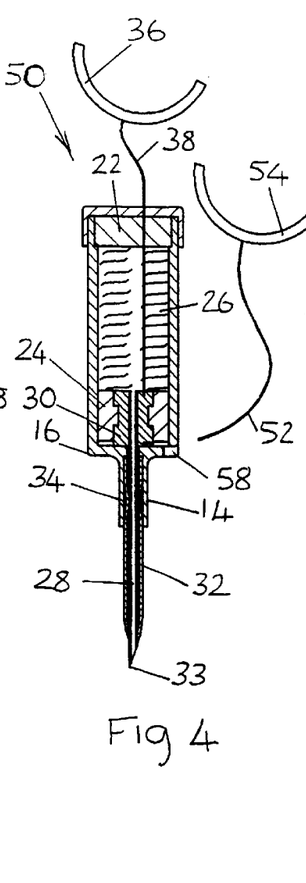
FIG. 4 is a view similar to FIG. 3 showing the apparatus after completion of the filling operation in which the needle assembly has been moved to the further position and the apparatus is ready to perform an injection.
Figure 5:
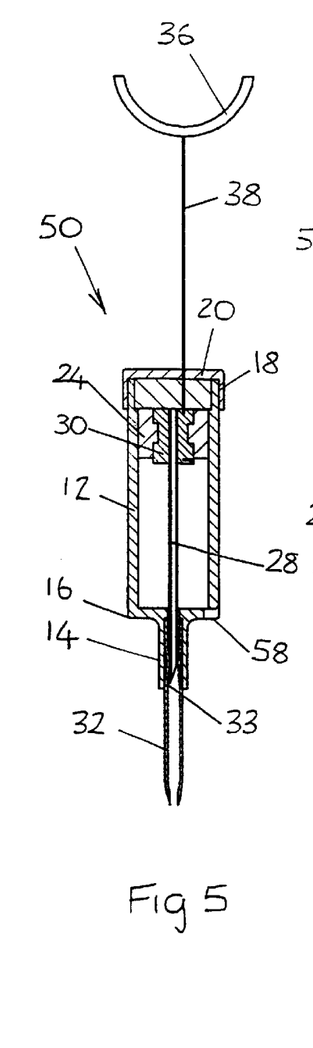
FIG. 5 is a view similar to FIG. 4 in which the injection apparatus is in a third position after having completed an injection of parenteral fluid and after the needle assembly has been re-retracted.

FIGS. 3, 4 and 5 show a parenteral apparatus 50 similar to that shown in FIGS. 1 and 2 with the addition of a filling means in the form of a second drawstring 52 and a second handle means 54. The drawstring 52 is inserted firmly into a substantially radial hole 56 in the hub 30.

Further the drawstring 52 extends from the hub 30 through an aperture 58 in the housing 12 at the first end 16 thereof and then to the handle means 54.

In use, the apparatus 50 is initially in the position and condition shown in FIG. 3. In this condition the apparatus 50 is empty. To fill the apparatus 50 with parenteral fluid, traction is applied manually to the drawstring 52 from the handle means 54 to move the seal 24 from adjacent the end 18 of the housing 12 towards the end 16 thereof. At this stage the catheter 32 would be located in a receptacle such as a glass ampoule containing parenteral fluid. The traction of the drawstring 52 causes the fluid to be drawn into the catheter 32 of the needle 28 as the resulting movement of the seal 24 tends to cause a vacuum within the housing 12.

The traction on the drawstring 52 is continued until the seal 24 and the hub 30 abut the end 16 of the housing 12 as shown in FIG. 4. At this stage the movement of the seal 24 has created the chamber 26 which is full of parenteral fluid similar to the condition shown in FIG. 1. At this point the drawstring 52 can be removed entirely as shown in FIG. 4 by simply pulling on the handle 54 laterally to so that the drawstring 52 leaves the radial hole 56 and can then be pulled through the hole 58. Subsequently, the apparatus 50 is used in the same manner as the apparatus 10, such that the seal 24 is moved to a position abutting the bung 22 and the needle tip 33 is housed within the boss 14 as shown in FIG. 5.

Figure 6:
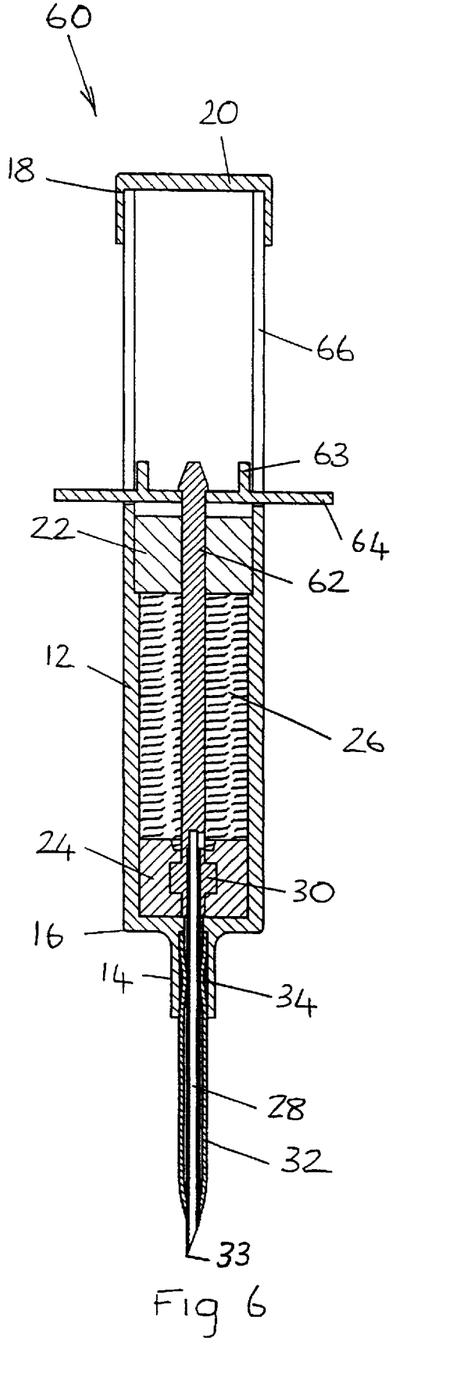
FIG. 6 is a longitudinal sectional view of a third embodiment of a parenteral apparatus in accordance with the present invention with a needle assembly in a first position ready to perform an injection.
Figure 7:
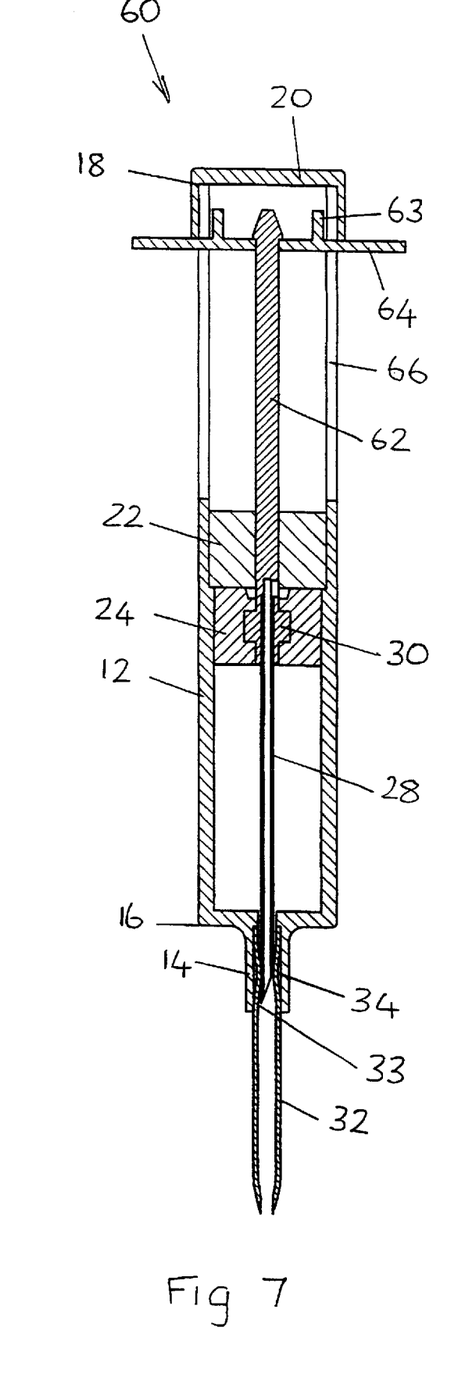
FIG. 7 is a view similar to FIG. 7 in which the parenteral apparatus is in a second position at the completion of an injection.
Figure 8:
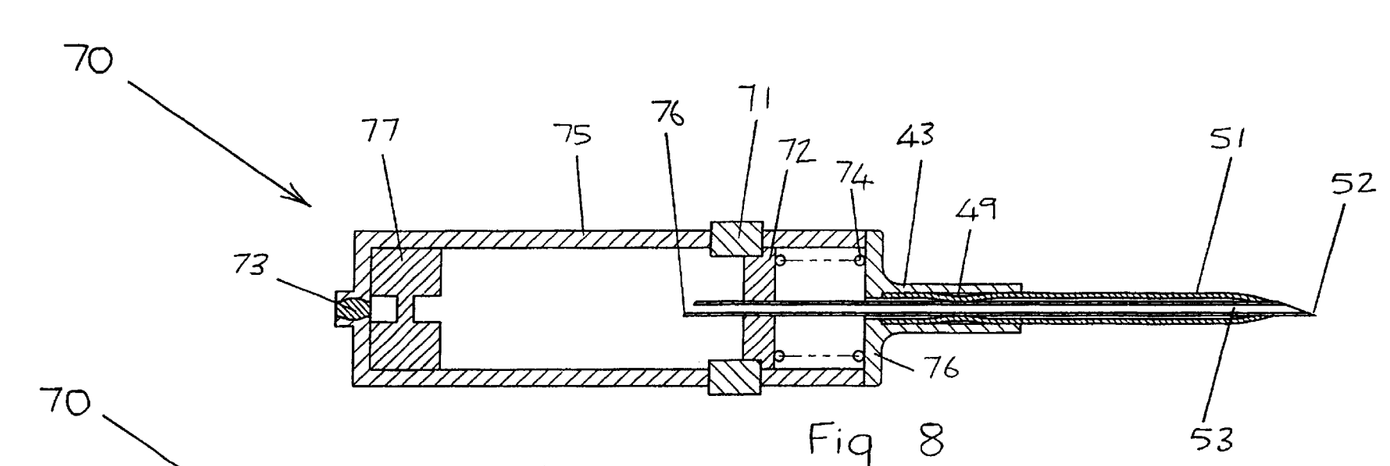
FIG. 8 is a longitudinal sectional view of a fourth embodiment of parenteral apparatus in accordance with the present invention ready to be filled by the introduction of parenteral fluid through a port in a body of the apparatus.

FIGS. 6 and 7 illustrate a parenteral apparatus 60 again very similar in action to the apparatus 10 but in this example a rigid rod 62 serves the function of the drawstring 38 and a handle means 63 including flat flanges 64 extending outwardly through longitudinal slots 66 in the housing 12 serve the function of the handle means 36.

As shown the rod 62 has a projection at its upper end as seen in FIGS. 6 and 7. The rod 62 passes through an aperture in the handle means 63 and the projection engages with the handle means 63 around the aperture.

If preferred the handle means 63 may be fixed to the rod 62 so that pressure on the flanges 64 acts to move the seal 24 from the position shown in FIG. 7 to the position shown in FIG. 6, so expanding the chamber 26 and, if the catheter 32 is immersed in fluid causing filling the chamber 26 with that fluid.

In use, the apparatus 60 is initially in the condition shown in FIG. 6 which is similar to that of the apparatus 10 in FIG. 1 except that the bung 22 is spaced from the end 18 and the body 12 has the slots 66 extending from adjacent the bung 22 to a position adjacent the end 18. In order to activate the apparatus 60 a similar procedure is followed as for the apparatus 10 except that the flanges 64 are manually moved towards the end 18 in the slots 66. This causes retraction of the rod 62 so that the seal 24 and the needle 28 move to the position shown in FIG. 7.

Further, it is envisaged that the apparatus of the present invention may be made difficult to refill. For example, in relation to FIGS. 6 and 7 the handle 64 may be arranged so that it is not fixed to the rod 62. Once the apparatus was in the position shown in FIG. 7 forward movement of the flange 64 would not cause corresponding movement of the rod 62 so that the apparatus could not readily be returned to the position shown in FIG. 6 and simultaneously refilled.

Further, it is envisaged that the apparatus 60 could be provided with a small opening, similar to the opening 58 described hereinbefore, to avoid the portion of the housing 12 between the seal 24 and the end being airtight.

FIGS. 8, 9, 10 and 11 illustrate a parenteral apparatus 70 which operates in a very similar manner to those shown in earlier figures but with the difference that action of moving the parts so as to transfer parenteral fluid from a chamber 46 to an injection site in tissue about an open end of a catheter 51 is effected by the action of a coiled spring 74. FIGS. 8 to 11 show a parenteral apparatus 70 having a housing 75 in the form of a substantially cylindrical barrel which provides a sealed chamber 46 between a closed second end and slidable seal 77. The closed end has a port sealed by a plug 73 fitted through a wall of the closed end. The plug 73 may be formed of elastomer such that the plug 73 may be readily pierced by a tube which may be used to inject fluid into the chamber 46 so as to fill the device and so that after removal of the filling tube the plug 73 will seal elastically. Alternatively, a filling tube may be introduced through a hole in a wall of the housing 75 in the position shown as 73 and after filling the hole may be sealed by a thermoplastic material, by gluing, by interference fit or by a welding procedure.

Figure 9:
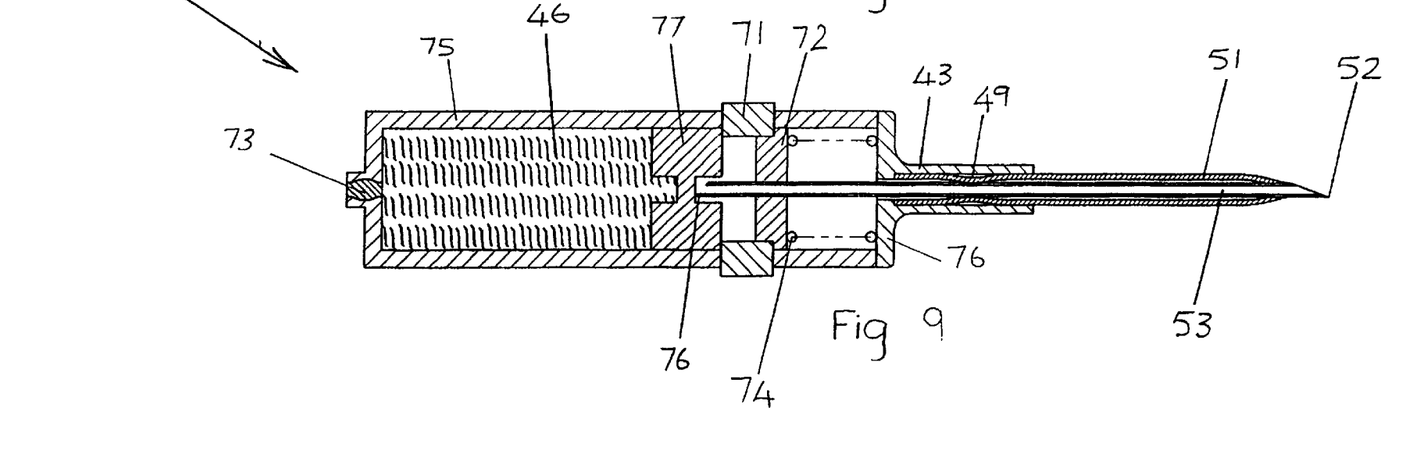
FIG. 9 is a view similar to FIG. 8 in which the parenteral apparatus is in a first position ready to pierce tissue and perform an injection.

FIG. 9 illustrates the parenteral apparatus 70 after filing. The introduction of fluid through the port 73 into the chamber 46 has moved axially the seal 77 hydraulically from the empty position shown in FIG. 8 to a full position shown in FIG. 9. It may be seen that the seal 77 is restrained from further axial movement by a retaining stop 71. The retaining stop 71 may be a circlip type arrangement fitted in transverse slots in the housing 75. Alternatively the stop 71 may be a removable plate similar to that shown in FIG. 15. The stop 71 may be an elliptical elastic ring fitted in transverse slots in the housing 75. Further, the compression of a long axis of the ellipse increases a short axis and moves the stop 71 clear of the flange 72, so allowing the flange 72 to move. The arrangement is preferably similar to that shown in FIG. 19. A needle 53 is sharpened at an outer end 52 also at an inner end 76. The needle 53 is fitted fixedly near its inner sharpened end 76 to a flange 72. The needle 53 extends through the flange 72. The flange 72 is in non-sealing engagement with an inner surface of the housing 75 and is able to slide freely axially but is restrained in the position shown in FIGS. 8 and 9 by the stop 71. The flange 72 is acted on by a coil spring 74 mounted in the housing 75 between an end 78 of the housing 75 and the flange 72. The coil spring 74 is shown compressed in FIGS. 8 and 9.

Figure 10:
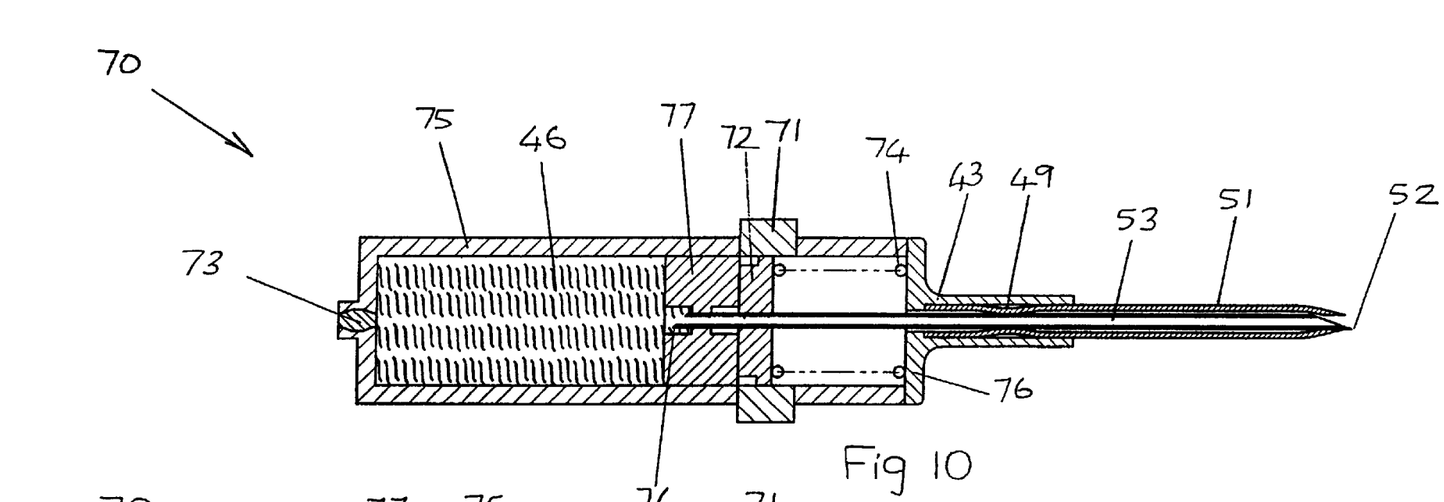
FIG. 10 is a view similar to FIG. 9 in which a retention means has been released and in which a needle has been retracted slightly so that an inner sharpened end of the needle has entered into fluid communication with parenteral fluid in the parenteral apparatus.
Figure 11:
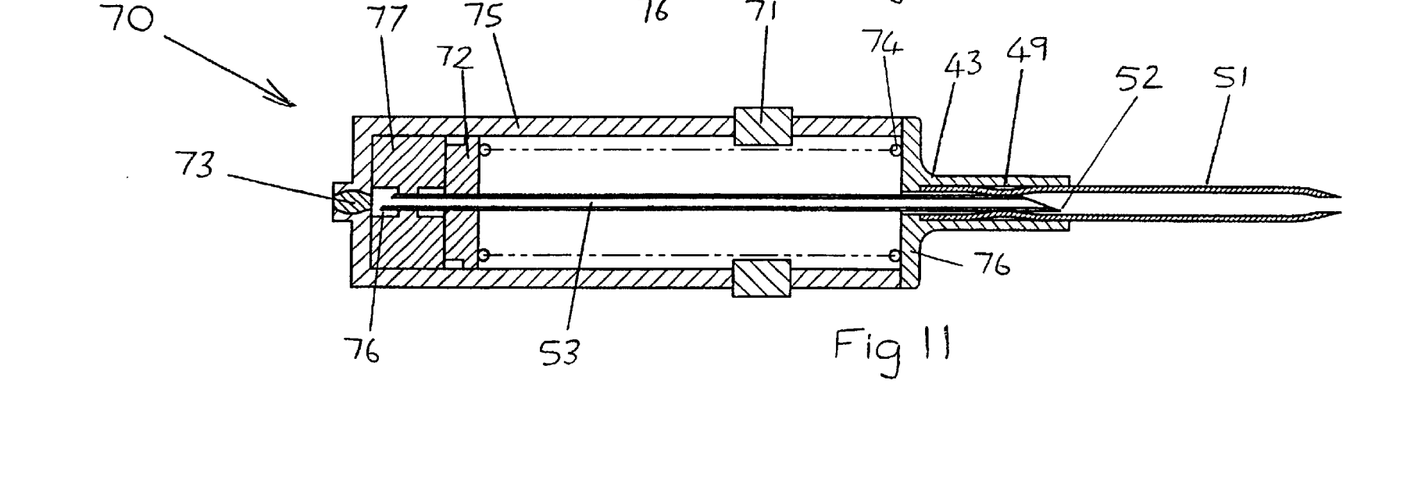
FIG. 11 is a view similar to FIG. 10 in which the parenteral apparatus is in a second position at the completion of an injection, ready for removal from tissue and for safe disposal.
Figure 12:
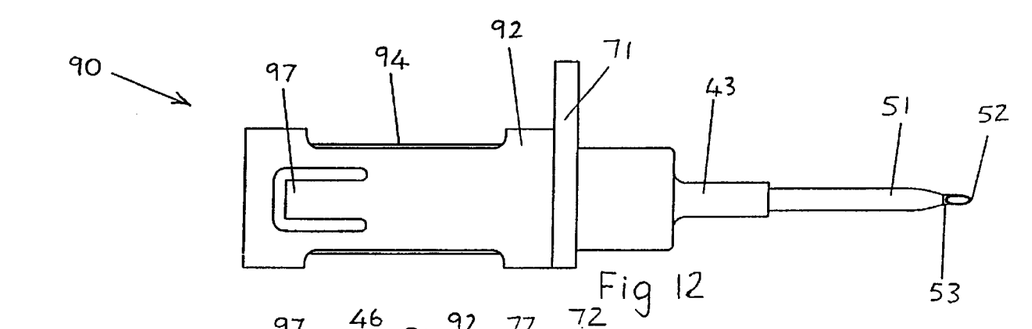
FIG. 12 is a side view of a fifth embodiment of a parenteral apparatus in accordance with the present invention shown in a first position.
Figure 13:
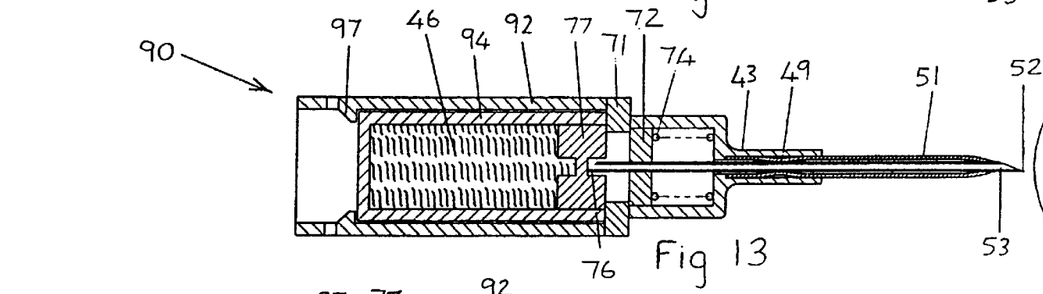
FIG. 13 is a longitudinal-sectional view of the fifth embodiment of the parenteral apparatus in accordance with the present invention shown in a first position showing a prefilled ampoule.

When the stop 71 is moved to a free position by an operator the spring 74, acting on the flange 72, drives the needle 53 towards the seal 77 and the inner sharpened end 76 of the needle 53 pierces the seal 77 so opening a fluid pathway between the chamber 46 and a lumen of the needle 53 as shown in FIG. 10. Further urging by the spring 74 drives the flange 72 and the seal 77 into the chamber 46 so driving the contents of the chamber 46 through the needle 53 and a catheter 51, so injecting the parenteral fluid in the chamber 46 into tissue in which catheter 51 may be located, at the same time retracting the needle 53 into a second position as shown in FIG. 11. Thus, the needle 53 remains in the fluid flow path from the position shown in FIG. 9 at which the sharp end 52 may perform an incision in tissue and the position shown in FIG. 11 at which all of the parenteral fluid has been removed from the chamber 46 through the needle 53. However, from the position shown in FIG. 10 onwards the needle 53 is progressively retracted so that the catheter 51 is also required to maintain the fluid flow path.

Figure 14:
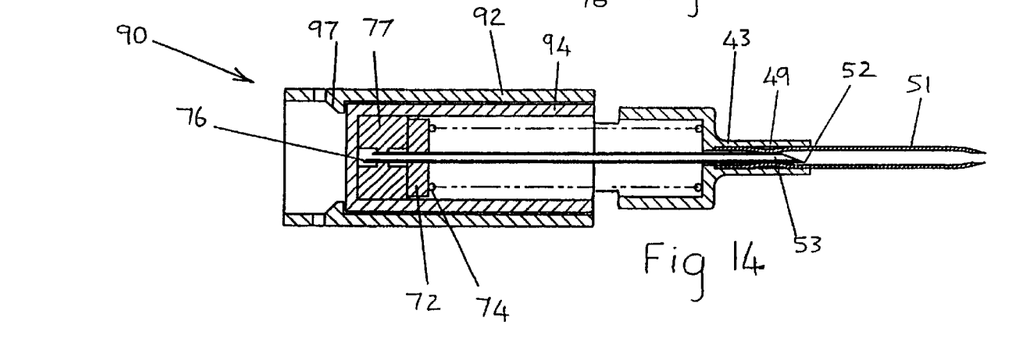
FIG. 14 is a view similar to FIG. 13 in which the parenteral apparatus is shown in a second position ready for disposal after having completed an injection by transfer of the contents of the ampoule to an injection site in tissue.
Figure 15:
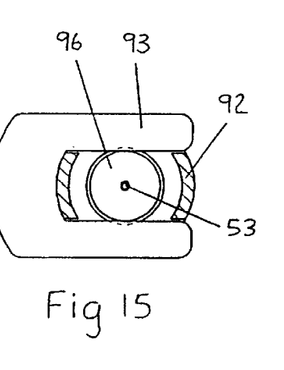
FIG. 15 is a cross-sectional view of a release means as shown in longitudinal sectional view in FIG. 13, in a position ready to be operated to release a spring which will initiate an injection sequence.

FIGS. 12, 13, 14 and 15 illustrate a parenteral apparatus 90, the structure and operation of which is generally similar to the parenteral apparatus shown in FIGS. 8 to 11 but with a major difference that the chamber 46 is removable and takes the form of a prefilled ampoule 94. The housing 92 takes the form of a short cylinder with a tubular boss 14 formed at one end. The boss 14 is fitted with a catheter 51 through which a needle 53 may slide sealingly. The housing 92 contains a coil spring 74 acting on a flange 72. The remainder of the housing 92 is not closed but takes the form of curved plates adapted to accommodate the prefilled ampoule 94, the interior of which forms the chamber 46. The ampoule 94 is initially closed by an axially slidable seal 77 inserted into an open end of the ampoule 94. To stabilise and retain the ampoule 94 in position the curved plates of the housing 92 are formed with at least two plastic springs 97. The springs 97 are profiled so as to have an outer chamfered face and an inner right angle face to form a ratchet. The ampoule 94 can slide past the springs 97, putting them under tension, but the ratchets prevent the ampoule 94 from moving out of the housing 12 once fitted. The flange 72 is acted on by the coil spring 74 but initially the flange 72 is restrained from moving by a retaining stop 71. FIG. 15 illustrates the parenteral apparatus 90 in transverse section and shows the retaining stop 71 in plan view. It can be seen that the retaining stop 71 is cut away so that it is well clear of the needle 53. FIG. 14 shows the parenteral apparatus 90 after removal of the retaining stop 71, so releasing the flange 72 and allowing the inner sharpened end 76 of needle 28 to pierce the seal 77 and open a fluid pathway from chamber 46 to the needle 53 and the catheter 51. Under the urging of the spring 74, the seal 77 moves into the chamber 46 causing the chamber 46 to empty through the needle 53 and catheter 51 so reaching the position shown in FIG. 14. As with FIGS. 8 to 11, the needle 53 remains in the fluid flow path as the chamber 46 is being emptied. However, as the needle 53 is withdrawn, the catheter 51 is also required to maintain the fluid flow path to tissue.

Figures 16, 17, 18, 19:
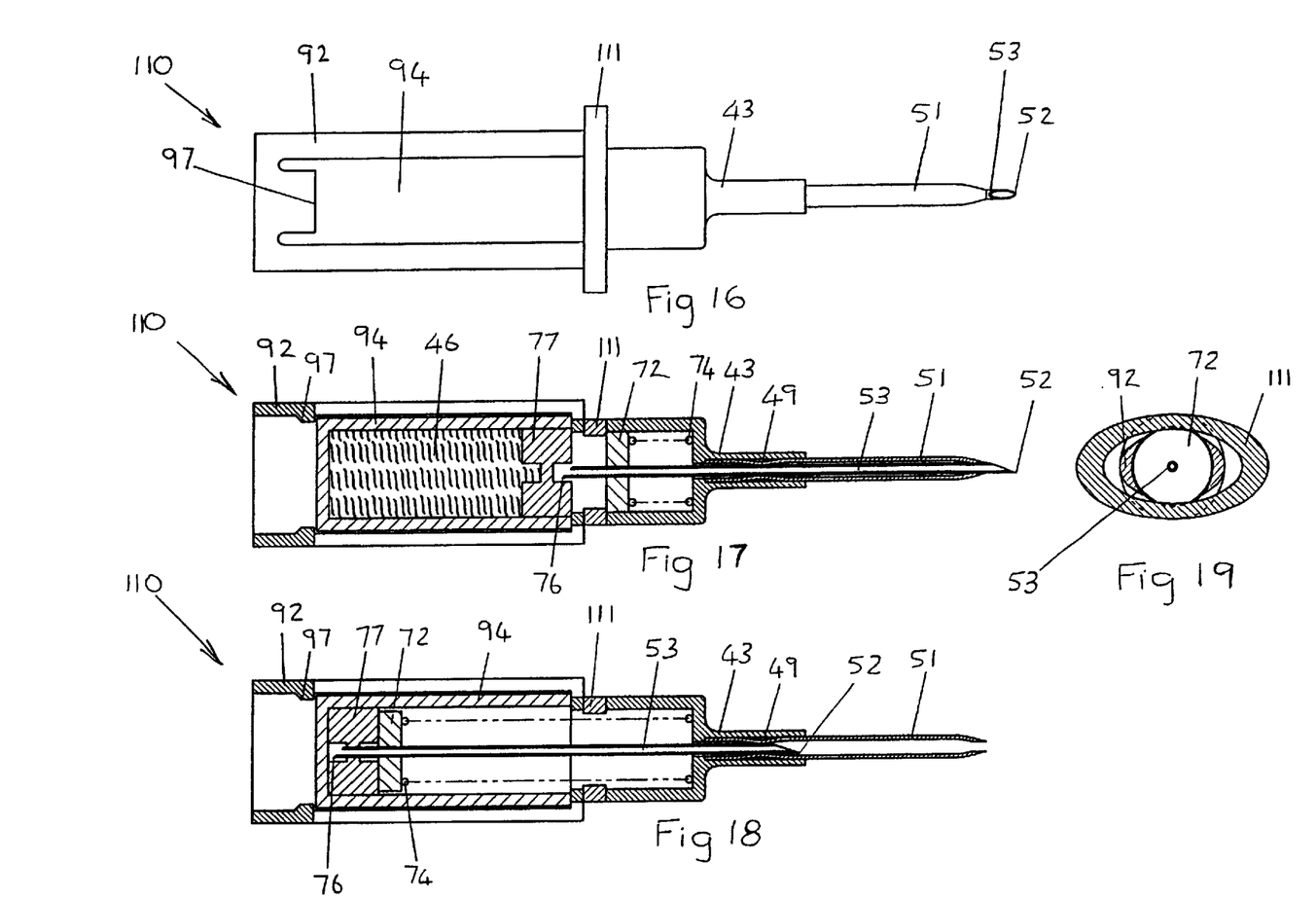
FIG. 16 is a side view of a sixth embodiment of a parenteral apparatus in accordance with the present invention shown in a first position with a fitted pre-filled ampoule seen through an aperture in a side wall.
FIG. 17 is a longitudinal-sectional view of the apparatus of FIG. 16 in a first position ready to perform an injection of fluid contained in the prefilled ampoule.
FIG. 18 is a view similar to FIG. 17 in which the parenteral apparatus is shown in a second position ready for safe disposal after having pierced a sliding seal in the fitted ampoule and pierced living tissue and having injected the contents of the ampoule.
FIG. 19 is a transverse section of a retaining means which prevents initiation of the injection sequence until compressed so as to change an elliptical shape to a near circular shape.

FIGS. 16, 17, 18 and 19 illustrate a parenteral apparatus 110 very similar to that shown in FIGS. 12, 13, 14 and 15 but differing in the construction of an ampoule 94 retaining spring on a housing and in the structure and operation of a restraining flange 72. In FIG. 16, a pre-filled ampoule 94 is seen through one open side of a housing. Opposing sides of an open end of the housing 12 have formed on them plastic springs 97 projecting inwardly a short distance from sides of the housing 12. The springs 97 have a ratchet shaped edge with faces as described hereinabove arranged to retain the fitted pre-filled ampoule 94 within the housing. Transverse slots are formed in a wall of the housing to accommodate a spring 111 which at rest is substantially elliptical (see FIG. 19). FIG. 19 shows the parenteral apparatus 110 in cross section and show the elliptical spring 111 in plan view. Squeezing a long axis of the spring 111 tends to change its shape to near circular and so move the walls defining a short axis outward so releasing restraint on the flange 72. Due to the urging of a compressed spring 74 acting on the flange 72 an inner sharpened end 76 of a needle 53 is driven through a seal 77 and the seal 77 is driven into a chamber 46, so delivering the contents of the ampoule 94 through needle 53 and catheter 51. FIG. 18 illustrates the parenteral apparatus in an empty position at the completion of an injection and ready for safe disposal.

FIGS. 20, 21, 22, 23 and 24 illustrate a parenteral apparatus 120 suitable for completely automatic injection of the contents of a pre-filled ampoule or prefilled parenteral apparatus and simultaneous retraction of the needle ready for disposal of the used device.

Figure 20:
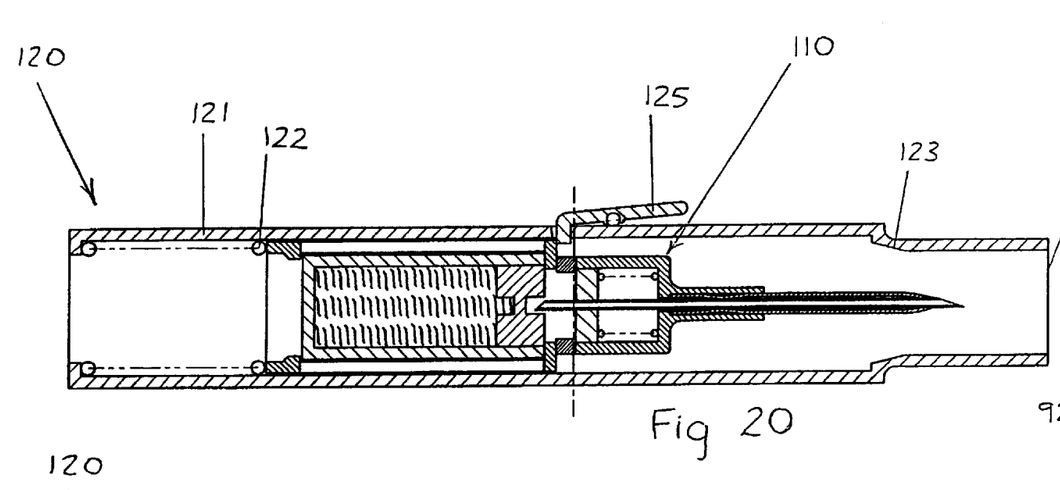
FIG. 20 is a longitudinal-sectional view of a seventh embodiment of a parenteral apparatus in accordance with the present invention in which an outer housing is fitted to allow the components similar to those described FIGS. 8 to 11 and FIGS. 16 to 18 to be moved axially in the housing toward tissue causing a needle and surrounding catheter to pierce the tissue and deliver parenteral fluid contents through the needle and catheter into the tissue.
Figures 21, 22:
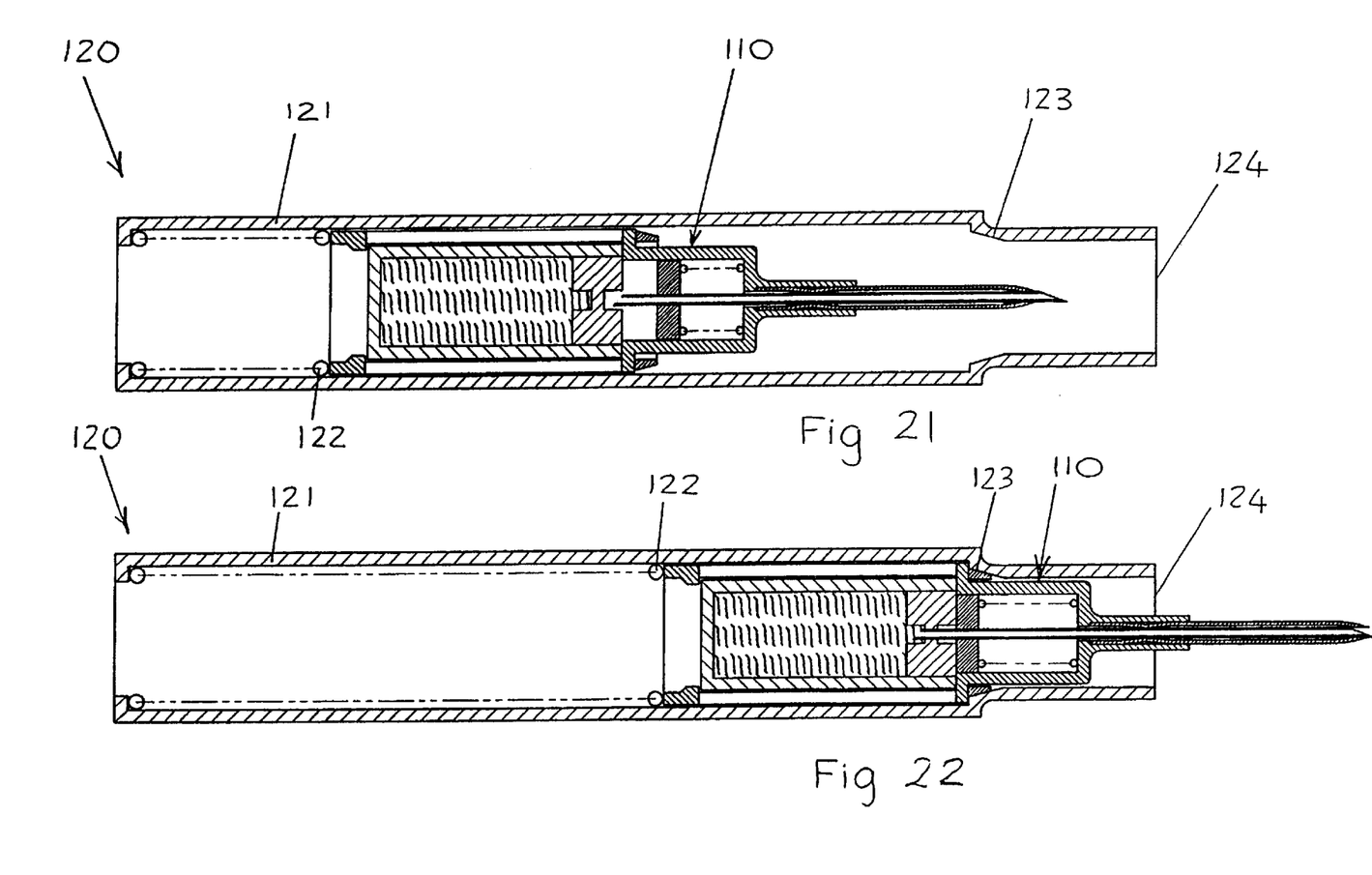
FIG. 21 is a 90° longitudinal section of the seventh embodiment as shown in FIG. 20.
FIG. 22 is a view similar to FIG. 21 in which a retaining means has been released so initiating an injection sequence by allowing an inner sharpened end of a needle to pierce a seal in a prefilled ampoule.
Figure 23:
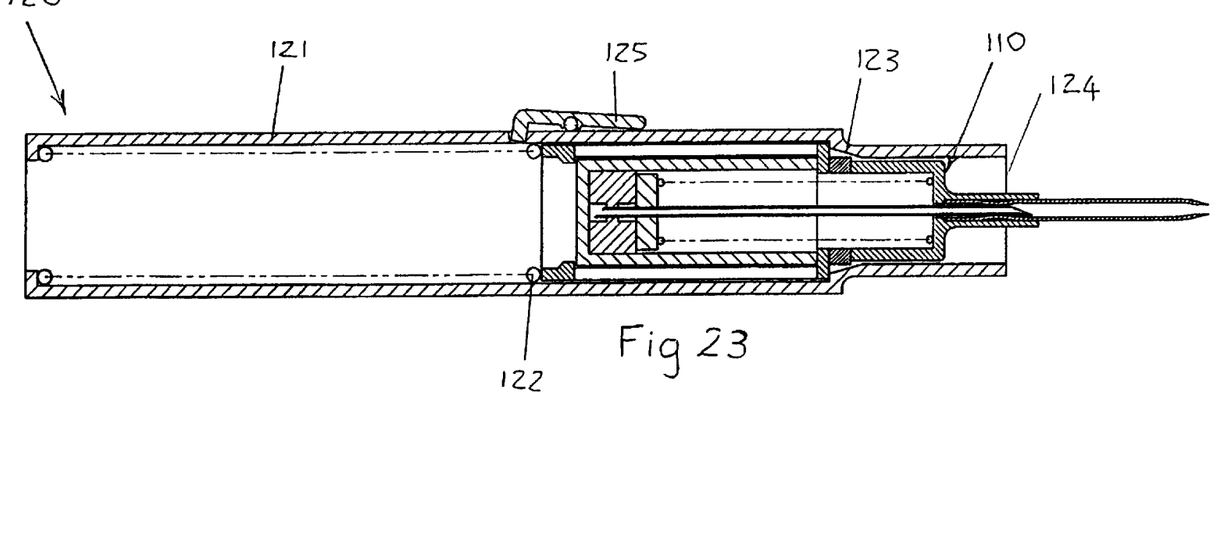
FIG. 23 is a view similar to FIG. 20 in which a latch fitted to a housing is in a released position and the parenteral apparatus is in a second position ready for safe disposal after having completed an injection of parenteral fluid.
Figure 24:
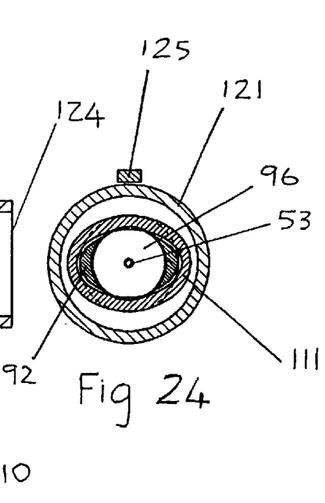
FIG. 24 is a cross-sectional view of an automatic release mechanism shown in a retaining position before movement of the parenteral apparatus to the position shown in FIG. 22.

FIG. 20 illustrates a parenteral apparatus 120 ready to perform an injection. The apparatus 120 has a substantially tubular outer housing 121 closed or partly closed at a relatively large end 122 by a cap or ring such that a parenteral device 110 or similar can be introduced into the outer housing 121. In an alternative arrangement the housing 121 may be in two parts joined for use approximately in the middle by a screw thread or latch. In another arrangement the housing 121 may be cut out on one side toward the end 122 to allow introduction of the parenteral device which can then be moved back against the tension of a spring 123 until the parenteral device engages a latch 125.

In FIG. 20, the parenteral apparatus 120 is shown assembled ready for use. A base of a chamber 46 is acted on by the spring 123 which is compressed whether by installing the parenteral apparatus 110 or by installing a cap (not shown) bearing the spring at the larger open end 122. A ring may be fitted to assist seating of the end of the spring 123 on the base of the chamber 46.

FIG. 20 illustrates a retaining latch 125 fitted to the housing 121 and acting on a flange 111 formed on the parenteral apparatus 110 so retaining its position in the housing 121 against the urging of the spring 123. An inner wall of the housing 121 against the urging of the spring 123. An inner wall of the housing 121 is constricted near an inner open end 124 to form a shoulder 126. Release of the latch 125 by finger pressure on a cantilevered arm thereof releases the parenteral apparatus 110 so that under the urging of the spring 123 the whole apparatus 110 moves axially in the housing 121 towards the inner open end 124. When an elliptical retaining stop 71 engages the shoulder 126 the stop 71 is forced into a substantially circular shape so lengthening a short axis of the ellipse and releasing a flange 72. At the same time any tissue adjacent to the open end 124 of the housing 121 is penetrated by a needle 53 and a catheter 51. Under further urging of a spring 74 the contents of chamber 46 are delivered through the needle 53 and the catheter 51 into the living tissue and the needle 53 is subsequently retracted ready for removal of the catheter 51 from the tissue and safe disposal of the parenteral apparatus 120. Other similar arrangements may be more suited to particular applications and in a preferred arrangement parenteral apparatus 70, pre-filled, may be fitted into the housing 121 to form the parenteral apparatus 120. Medication could then be supplied to a patient in the parenteral apparatus 70 in the housing 121 and self injected according to medical advice. Such an arrangement would also be useful to provide emergency parenteral medication.

For example, the apparatus of the present invention could be provided filled using special equipment available to manufacturing pharmacists.

Modification and variations such as would be apparent to a skilled addressee are deemed within the scope of the present invention. For example, it is envisaged that the catheter could be moveable relative to the remainder of the apparatus whilst the needle remains stationary relative to the rest of the apparatus.

What is claimed is:

1. A parenteral apparatus characterised by a housing having a first end and a second end and defining a chamber for parenteral fluid, a thin walled catheter having a free end closely enclosing a tubular needle having a sharp point, the catheter being mounted to the housing, the needle and the catheter being longitudinally moveable relative to one another between a first position at which the needle extends from the catheter so that the sharp point is exposed and a second position at which the sharp point is located within the catheter, the needle remaining in a fluid pathway of the parenteral apparatus at all times between the first and second positions, the sharp point of the needle being arranged to pierce tissue when the catheter and the needle are in their relative first position and retraction means being provided for moving the needle and catheter relatively from the first position to the second position, wherein as the needle and catheter are moved relatively from the first position to the second position fluid contained in the housing is initially expelled through the catheter.

2. A parenteral apparatus according to claim 1, characterised in that as the needle is retracted towards the second position the catheter also forms part of the fluid pathway and fluid is also expelled through the catheter.

3. A parenteral apparatus according to claim 1, characterised in that the housing has a forwardly protecting tubular boss in which the catheter is mounted and within which the sharp point of the needle is located in the second position of the needle and the catheter.

4. A parenteral apparatus according to claim 1, characterised in that the housing is closed off at the second end thereof so as to define an end of the chamber, and an axially slidable seal is located in the housing so as to define a further end of the chamber.

5. A parenteral apparatus according to claim 4, characterised in that the needle is mounted to and extends through the seal, the seal being disposed adjacent a first end of the housing in the first position the catheter and the needle and adjacent a second end of the housing in the second position thereof, the seal being operatively connected to the retraction means.

6. A parenteral apparatus according to claim 4, characterised in that the retraction means includes a flexible elongate member operatively connected to the seal and extending to a point external of the housing.

7. A parenteral apparatus according to claim 6, characterised in that the flexible elongate member is connected at an outer end thereof to a handle means.

8. A parenteral apparatus according to claim 1, characterised in that the apparatus has an initial position in which the sharp point of the needle is located within the housing and the seal is located remote from the first end of the housing, and means is provided for pulling the seal forwardly towards the first end of the housing whilst the catheter is immersed in a parenteral fluid so as to cause the fluid to be drawn into the chamber of the housing.

9. A parenteral apparatus according to claim 8, characterised in that the means for pulling the seal forwardly includes a flexible elongate member operatively connected to the seal and extending to a point external of the housing.

10. A parenteral apparatus according to claim 9, characterised in that the flexible elongate member is connected at an outer end thereof to a handle means.

11. A parenteral apparatus according to claim 1, characterised in that the needle has an inner end located within the housing at all times, the inner end of the needle having a sharp point and being initially spaced from the seal, means being provided for urging the needle towards the seal as the needle and catheter move to their second relative position, so that the inner end of the needle pierces the axially slidable seal and the seal is subsequently pushed into the housing so as to expel fluid therefrom.

12. A parenteral apparatus according to claim 11, characterised in that the housing, in use, includes a prefilled separate ampoule, the ampoule containing the axially slidable seal.

13. A parenteral apparatus according to claim 11, characterised in that the means for urging the needle towards the seal includes a spring means acting on a flange attached to the needle, the flange also acting to urge the axially slidable seal into the housing.

14. A parenteral apparatus according to claim 13, characterised in that there is provided a latch means for spacing the needle and flange initially away from the seal, the latch means being manually operable so as to release the needle and flange and allow them to be urged towards the seal.

15. A parenteral apparatus according to claim 14, in which the latch means includes a flexible elliptical member having a long axis whereby upon the elliptical member being manually squeezed the needle and flange are released.

16. A parenteral apparatus according to claim 14, in which the latch means is a plate member whereby upon the plate member being manually withdrawn the needle and flange are released.

17. A parenteral apparatus according to claim 11, which is arranged to be mounted in an outer housing with the sharp needle point within the outer housing, the parenteral apparatus being retained in the outer body, and latch means being provided, whereby upon manual release of the latch means the parenteral apparatus is urged towards a shoulder within the outer housing and the sharp point of the needle is extended from the outer housing so as to be able to pierce tissue, and upon contact with the shoulder the needle is released automatically so as to pierce the seal by means of the sharp point at the inner end and then the seal is pushed into the housing so that fluid is expelled from the housing through the needle initially and through the needle and catheter subsequently.

* * * * *